US006270966B1

(12) United States Patent
Weinstein et al.

(10) Patent No.: US 6,270,966 B1
(45) Date of Patent: Aug. 7, 2001

(54) RESTRICTION DISPLAY (RD-PCR) OF DIFFERENTIALLY EXPRESSED MRNAS

(75) Inventors: John N. Weinstein, Chevy Chase, MD (US); John Buolamwini, Oxford, MS (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/130,079

(22) Filed: Aug. 7, 1998

Related U.S. Application Data

(63) Continuation of application No. PCT/US97/02009, filed on Feb. 7, 1997.
(60) Provisional application No. 60/011,379, filed on Feb. 9, 1996.

(51) Int. Cl.[7] .............................. C12Q 1/68; C12Q 1/48; C12P 19/34; C07H 21/04

(52) U.S. Cl. .............................. 435/6; 435/15; 435/91.2; 435/91.5; 435/91.51; 435/91.52; 536/24.2; 536/24.33

(58) Field of Search .............................. 435/6, 15, 91.2, 435/91.5, 91.51, 91.52; 536/24.2, 24.3, 24.33, 25.3

(56) References Cited

U.S. PATENT DOCUMENTS

| | | | |
|---|---|---|---|
| 5,102,785 | * 4/1992 | Livak et al. | 435/6 |
| 5,213,961 | 5/1993 | Bunn et al. | 435/6 |
| 5,382,511 | 1/1995 | Stapleton | 435/6 |
| 5,459,037 | 10/1995 | Sutcliffe et al. | 435/6 |
| 5,525,486 | 6/1996 | Honjo et al. | 435/69.1 |
| 5,599,672 | 2/1997 | Liang et al. | 435/6 |
| 5,599,696 | 2/1997 | Mueller et al. | 435/91.2 |
| 5,618,702 | 4/1997 | Scanlon | 435/91.2 |
| 5,643,730 | 7/1997 | Banker et al. | 435/6 |
| 5,643,765 | 7/1997 | Willey | 435/91.2 |
| 5,643,766 | 7/1997 | Scheele et al. | 435/91.2 |
| 5,656,462 | 8/1997 | Keller et al. | 435/91.2 |

(List continued on next page.)

FOREIGN PATENT DOCUMENTS

| | | |
|---|---|---|
| 0 607 054 | 7/1994 | (EP) . |
| 91 15601 | 10/1991 | (WO) . |
| 93/06239 | * 3/1993 | (WO) . |
| 93 18176 | 9/1993 | (WO) . |
| WO 94/01582 | 1/1994 | (WO) . |
| 95 13369 | 5/1995 | (WO) . |
| WO 97/17466 | 5/1997 | (WO) . |

OTHER PUBLICATIONS

Ivanova, N.B. et al. Molecular Biology 28(6):848–853, Dec. 1994.*
Suzuki, H. et al, Nucleic Acids Research 24(2):289–294, Jan. 1996.*
Vos, P. et al, Nucleic Acids Research 23(21):4407–4414, Nov. 1995.*

(List continued on next page.)

*Primary Examiner*—Carla J. Myers
*Assistant Examiner*—Diana Johannsen
(74) *Attorney, Agent, or Firm*—Knobbe, Martens, Olson & Bear, LLP

(57) ABSTRACT

A method for detecting gene expression in cells by reverse transcribing mRNA molecules into cDNA, cutting the cDNA with at least one restriction endonuclease, adding adaptor sequences to the cDNA fragments and selectively amplifying a subset of the cDNA by a polymerase chain reaction (PCR) to present a two-dimensional display of the DNA fragments or for cloning the DNA fragments into a vector is disclosed. In one embodiment, cDNA corresponding to the 3' end of the mRNA is amplified and displayed or cloned, whereas in another embodiment, cDNA corresponding to the entire mRNA molecule is amplified and displayed or cloned.

13 Claims, 2 Drawing Sheets

U.S. PATENT DOCUMENTS

| | | | |
|---|---|---|---|
| 5,665,544 | 9/1997 | Chenchik et al. | 435/6 |
| 5,665,547 | 9/1997 | Pardee et al. | 435/6 |
| 5,712,126 | 1/1998 | Weissman et al. | 435/91.2 |
| 5,716,785 | 2/1998 | Van Gelder et al. | 435/6 |
| 5,814,445 * | 9/1998 | Belyavsky | 435/6 |

OTHER PUBLICATIONS

Tracy, T.E. et al. BioTechniques 11(1):68–75, Jul. 1991.*

Ahern, H. The Scientist 9(15):20, Jul. 1995.*

Ausubel, et al., eds., *Short Protocols in Molecular Biology*, John Wiley & Sons, pp. 75–76, Copyright 1989, "Analysis of DNA Sequences by Blotting and Hybridization."

Ausubel, et al., eds., *Short Protocols in Molecular Biology*, John Wiley & Sons, pp. 133–135, Copyright 1989, "Construction of Hybrid DNA Molecules."

Cecchini, et al., *Nulcleic Acids Research*, 21(24):5742–5747, 1993, "Identification of genes up–regulated in dedifferentiating *Nicotania glauca* pith tissue, using an improved method for constructing a subtractive cDNA library."

Chencik, et al., *BioTechniques*, 21:526–534, Sep. 1996, "Full–Length cDNA Cloning and Determination of mRNA 5' and 3' Ends by Amplification of Adaptor–Ligated cDNA."

Debuire, et al., *Clinical Chemistry*, 41(6):819–825, 1995, "Nonisotopic Competitive RT–PCR Assay to Measure MDR1 Gene Expression."

Dianchenko, et al., *Biochemical and Biophysical Research Communications*, 219(0317):824–828, 1996, "Combining the Technique of RNA Fingerprinting and Differential Display to Obtain Differentially Expressed mRNA."

Duguid, John R., and Mary C. Dinauer, *Nucleic Acids Research*, 18(9):2789–2792, Received 9/89, Accepted 12/89, "Library subtraction of in vitro cDNA libraries to identify differentially expressed genes in scrapie infection."

Kato, Kikuya, *Nucleic Acids Research*, 23(18):3685–3690, 1995, "Description of the entire mRNA population by a 3' end cDNA fragment generated by class IIS restriction enzymes."

Kato, Kikuya, *Nucleic Acids Research*, 24(2):394–395, 1996, "RNA fingerprinting by molecular indexing."

Ko, Minoru S.H., *Nucleic Acids Research*, 18(19):5705–5711, 1990 "An 'equalized cDNA library' by the reassociation of short double–stranded cDNAs."

Lee, Youn–Ho and Victor D. Vacquier, *Analytical Biochemistry*, 206:206–207, 1992, "Reusable cDNA Libraries Coupled to Magnetic Beads."

Liang, et al., *Nucleic Acids Research*, 21(14):3269–3275, 1993, "Distribution and cloning of eukaryotic mRNAs by means of differential display: refinements and optimization."

Liang, et al., *Nucleic Acids Research*, 22(25):5763–5764, 1994, "Differential display using one–base anchored oligo–dT primers."

Lisitisyn, et al., *Science*, 259:946–951, Feb. 12, 1993, "Cloning the Differences Between Two Complex Genomes."

Navarro, et al., *Journal of Virological Methods*, 56:59–66, 1996. "A general strategy for cloning viroids and other small circular RNAs that uses minimal amounts of template and does not require prior knowledge of its sequence."

Rickwood, D. and B.D. Hames, eds., *Gel Electrophoresis of Nucleic Acids*, 2nd Edition, Oxford University Press, pp. 182–200, Copyright 1990.

Siebert, Paul D. and Aaron Apte, *CLONTECHniques*, vol. VIII, No. 1, pp. 1–3, Jan. 1993, "A New Method for Amplification of 5'–cDNA Ends."

Sokolov, Boris P. and Darwin J. Prockop, *Nucleic Acids Research*, 22(19):4009–4015, 1994, "A rapid and simple PCR–based method for isolation of cDNAs from differentially expressed genes."

Wang, Zhou and Donald D. Brown, *Proc. Natl. Acad. Sci. USA*, 88:11505–11509, Dec. 1991, "A gene expression screen."

Zeng, et al., *Nucleic Acids Research*, 22(21):4381–4385, 1994, "Differential cDNA cloning by enzymatic degrading subtraction (EDS)."

Promega Corporation, *Information Brochure*, "Molecular Biology/Reagent Systems," pp. 164, 182–183, date unknown, "Lightsmith™ I Luminescence Engineering Systems for Oligonucleotides," and "RiboClone® EcoR I Linker Ligation Systems."

Promega Corporation, *Promega Protocols and Applications Guide*, pp. 17–33, 35–43, Copyright Mar. 1991, "Restriction Enzymes and Linkers."

Biotechniques vol. 18; No. 5, 1995, pp. 842–850, , XP002033062, Ayala M. et al., : "New primer strategy improves precision of differential display" cited in the application see whole document esp. p. 846, 3 column, 3. para.

PCR Methods & Applications, vol. 4, No. 3, Dec. 1, 1994, pp. 160–166, XP000490933, Samar Hamoui, et al., "Quantitation of MRNA Species by RT–PCR on Total MRNA Population".

Science, vol. 257, No. 5072, Aug. 14, 1992, pp. 967–971, XP000508268, Liang et al.: "Differential Display of Euraryotic Messenger RNA by Means of the Polymerase Chain Reaction".

* cited by examiner

```
                            SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
         (A) LENGTH: 19 base pairs
         (B) TYPE: nucleic acid
         (C) STRANDEDNESS: single
         (D) TOPOLOGY: linear (ii) MOLECULE TYPE: mRNA (xi) SEQUENCE DESCRIPTION: SEQ ID NO:1:

NBAAAAAAAA AAAAAAAAA                                                     19

(2) INFORMATION FOR SEQ ID NO:2:

(i) SEQUENCE CHARACTERISTICS:
         (A) LENGTH: 42 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

GGCCACGCGT CGACTAGTAC NNVTTTTTTT TTTTTTTTTT VN                           42

(2) INFORMATION FOR SEQ ID NO:3:

(i) SEQUENCE CHARACTERISTICS:
         (A) LENGTH: 6 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

GATCNN                                                                    6

(2) INFORMATION FOR SEQ ID NO:4:

(i) SEQUENCE CHARACTERISTICS:
         (A) LENGTH: 6 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

NNGATC                                                                    6

(2) INFORMATION FOR SEQ ID NO:5:

(i) SEQUENCE CHARACTERISTICS:
         (A) LENGTH: 42 base pairs
         (B) TYPE: nucleic acid
```

(C) STRANDEDNESS: single
        (D) TOPOLOGY: linear (ii) MOLECULE TYPE: cDNA (xi) SEQUENCE DESCRIPTION: SEQ ID NO:5:

NBAAAAAAAA AAAAAAAAG NNBTACTAGT CGACGCGTGG CC                              42

(2) INFORMATION FOR SEQ ID NO:6:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGCCACGCGT CGACTAGTAC NNVTTTTTTT TTTTTTTTTT VN                             42

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCCGGTGCGG TCGACAT                                                        17

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

GATCATGTCG ACCGCACCGG                                                     20

(2) INFORMATION FOR SEQ ID NO:9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TCCGGTGCGG TCGACATGAT CNN                                                 23

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

NNGATCATGT CGACCGCACC GG                                                    22

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

CCGGTGCGGT CGACATGATC NN                                                    22

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

GGCCACGCGT CGACTAGTAC NN                                                    22

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

NNGATCATGT CGACCGCACC GGA                                                   23

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

GGCCACGCGT CGACTAGTAC NNCTTTTTTT TTTTTTTTTT VN                              42

(2) INFORMATION FOR SEQ ID NO:15:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GGCCACGCGT CGACTAGTAC NNCTTTTTTT TTTTTTTTTT CG                              42

(2) INFORMATION FOR SEQ ID NO:16:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

GGCCACGCGT CGACTAGTAC NNCTTTTTTT TTTTTTTTTT GC                42

(2) INFORMATION FOR SEQ ID NO:17:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

CCGGTGCGGT CGACATGATC GC                                   22

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

CCGGTGCGGT CGACATGATC CG                                   22

(2) INFORMATION FOR SEQ ID NO:19:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

GGCCACGCGT CGACTAGTAC VN                                   22

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GGCCACGCGT CGACTAGTAC CG                                   22

(2) INFORMATION FOR SEQ ID NO:21:

```
    (i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:21:

GGCCACGCGT CGACTAGTAC GC                                            22

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

GATCCACACC AGCCAAACCC A                                             21

(2) INFORMATION FOR SEQ ID NO:23:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:23:

GGTTTGGCTG GTGTG                                                    15

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:24:

GTTTGGCTGG TGTGGATCAA                                               20

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:25:

GTTTGGCTGG TGTGGATCAT                                               20
```

RESTRICTION DISPLAY (RD-PCR) OF DIFFERENTIALLY EXPRESSED MRNAS This application is a continuation of International Application No. PCT/US97/02009 filed Feb. 7, 1997, which claims the benefit of priority of U.S. application Ser. No. 60/011,379, filed Feb. 9, 1996.

The present invention relates to a method of detecting and characterizing gene expression in cells, and specifically relates to a method of detecting a population of mRNA molecules by transcribing the mRNA into complementary DNA (cDNA) molecules, restriction cutting the DNA, adding adaptor DNA sequences, amplifying the cDNA molecules by a polymerase chain reaction (PCR) and detecting the amplified cDNA.

BACKGROUND OF THE INVENTION

Mammalian cells each generally express approximately 15% of the total of about 100,000 genes under normal physiological conditions. Gene expression results in about 15,000 individual mRNA species per cell, of which about 1% represent expression unique to a cell type or to a cell's developmental or physiological state. The relatively or almost unique expression of a minority of genes in cells of interest compared with other cells is referred to as differential expression and has been used to classify cells based on their mRNA content. For example, different types of tumor cells may be classified and compared with normal cells based on differential expression of oncogenes.

Because differential expression of genes can be used to characterize cells based on their mRNA content, investigators have developed methods to monitor differential expression of a population of cells. Many methods rely on subtractive RNA hybridization techniques (Lee et al., *Proc. Natl. Acad. Sci. USA* 88: 2825–2830, 1991). More recently, a method of differential display of eukaryotic mRNA following reverse transcription into DNA and amplification by a polymerase chain reaction (PCR) has been developed to visualize subsets of molecules on a gel (Liang, P. and Pardee, A. B., *Science* 257:967–71, 1992). Methods of this type are herein referred to as differential display-polymerase chain reaction (DD-PCR) techniques.

Liang and Pardee described a method of separating and displaying individual mRNA species called the DD-PCR technique (for differential display-polymerase chain reaction). In this method, mRNA isolated from eukaryotic cells is reverse transcribed into cDNA, which is then selectively amplified using a series of primers in PCR. The primer for the first strand synthesis contains an oligo-dT sequence anchored by the addition of two bases at the 3' end of the primer (e.g., 5' $T_{11}CA$ 3'). The second strand primer used in PCR amplification is either a selected sequence specific for a known gene or any arbitrary oligonucleotide capable of priming a PCR. The amplified sequences correspond to the 3' end of the expressed genes. PCR amplification is done in the presence of a radiolabeled nucleotide (e.g., ATP labeled at the α position with $^{35}S$) and the amplified radioactive molecules are separated as single stranded molecules on a denaturing DNA sequencing gel. They are then visualized by autoradiography. About 50–100 bands (of up to about 500 bp in size) of the reverse transcribed and amplified mRNA are displayed. This visual display of the differentially expressed subset of genes is called a differential display. The pattern of a differential display is characteristic of the cell type analyzed, the cell physiology when the mRNA was isolated, the species from which the cells were derived and the primers used in PCR amplification. Thus, a differential display can be used to distinguish cell types based on their mRNA content, similar to the characterization of cells by DNA fingerprinting.

By amplifying aliquots of RNA with oligo-dT primers differing in the two additional 3' bases, the total mRNA can be amplified in twelve subsets (e.g., primer 5' $T_{11}CA$ 3' to amplify one subset, primer 5' $T_{11}GA$ 3' to amplify another subset, etc.). Each subset results in its own unique differential display pattern obtained using the same source of mRNA. Bands of interest can be eluted from the gel and used as probes, DNA sequenced or cloned using conventional methods.

The original DD-PCR method has been further refined to include other anchored primers and optimized conditions for PCR (Liang, P., et al., *Nucleic Acids Res.* 21: 3269–3275, 1993). The optimized anchored oligo-dT primer is degenerate, comprising 5' $T_{12}MN$ 3', where M can be A, C or G, but not T, and N can be any of the four possible deoxynucleotides (T, A, C or G). Both M and N are essential to anchor the primer to the end of the poly(A) tail of the mRNA, but N lends specificity to the primer. By using a mixture of primers degenerate at the M position, the number of PCR reactions for the differential display of an RNA sample can be decreased to three instead of twelve. DNA-free RNA, either total cellular RNA or mRNA, can be used. Cloning of the amplified fragments is achieved by eluting bands of interest from the display gel, amplifying them again by PCR and cloning them into a vector. An eluted band, reamplified by PCR, can be used to probe RNA blots to identify PCR fragments that hybridize to the RNA of interest to improve the probability of isolating the clones of interest (Utans, U. et al., *Proc. Natl. Acad. Sci. USA* 91: 6463–6467, 1994).

Other modifications of the DD-PCR method include the use of a nondenaturing gel to detect double stranded DNA fragments (Bauer, D., et al., *Nucleic Acids Res.* 21: 4272–4280, 1993). Dye-labeled primers can be used in place of a radiolabeled primer in the PCR reactions so that the amplified fragments can be detected by using an automated DNA sequencing machine (Bauer, D., et al., *Nucleic Acids Res.* 21: 4272–4280, 1993; Ito, T. et al., *FEBS Lett.* 351: 231–236, 1994).

Another modification of the DD-PCR procedure, useful for analyzing in vivo samples, employs hybridization to immobilized RNA or to immobilized plasmid DNA, followed by direct PCR sequencing of the DNA (Mou, et al., *Biochem. Biophys. Res. Commun.* 199: 564–569, 1994). These hybridization steps selectively display a cDNA of interest instead of displaying the entire population of amplified fragments resulting from the DD-PCR reactions.

In addition to DD-PCR, other methods of RNA amplification using reverse transcription and PCR are known. U.S. Pat. No. 5,104,792 discloses a method of nucleic acid amplification using "universal" primers having identical 5' end sequences but degenerate 3' end sequences. The degenerate 3' sequences anneal to the nucleic acid of interest at random sites, and the 5' identical ends are used subsequently in sequencing, cloning or other standard molecular genetic manipulations. After two or more rounds of extension with these primers, the 3' degenerate primers are removed. The sequences are then amplified by PCR using primers in which the 3' sequence is identical to the 5' end non-degenerate sequence of the universal primer set.

The published abstract (available from Derwent World Patents Index, Derwent Info Ltd.) of U.S. patent application Ser. No. 7,669,731 discloses a method of detection of RNA sequences using reverse transcription and PCR. This technique specifically amplifies mRNA sequences without amplifying contaminating DNA sequences, allowing for detection of sequences present in the mRNA. In this method, the primer for reverse transcription of mRNA molecules contains a unique, random nucleotide sequence for "tagging" the cDNA strands. Then, a second primer that anneals to the tagged cDNA at a position upstream of the first primer is used to extend the sequence at a temperature that does not allow hybridization of the first primer.

One method of detecting differential gene expression relies on subtractive hybridization of PCR-amplified cDNA (Hubank, M. and Schatz, D. G., *Nucleic Acid Res.* 22: 5640–5648, 1994). This method, called representational difference analysis, is a modification of a method used to screen differences in genomic DNA. In this method, mRNA is reverse transcribed into cDNA, which is cut with a restriction enzyme. An adaptor sequence is ligated to the cut ends to serve as a hybridization site for appropriate PCR primers, and the fragments are PCR amplified (producing the "tester" DNA). The fragments are then hybridized with an excess of another cDNA population (the "driver" DNA) which does not have adaptor sequences and therefore is not amplified during subsequent PCR amplification. During the PCR, homoduplexes of driver-driver DNA and heteroduplexes of driver-tester DNA are not amplified. Only homoduplexes of tester-tester DNA (with adaptor sequences on both strands) are exponentially amplified in subsequent PCR reactions. Successive iterations of the subtractive hybridization and PCR process selectively amplify fragments representative of mRNA unique to the source of the "tester" cDNA.

PCT International Application WO 93/24655 describes another method of detecting differential expression by generating a fingerprint for the RNA. This method uses a primer and a terminator nucleotide (e.g., dideoxynucleoside triphosphate) in a cDNA extension process that produces about 10 to 60 bands per reaction. Each band represents a cDNA oligonucleotide beginning at the primer and terminating at the site of incorporation of the terminator nucleotide. The bands are separated by electrophoresis on a denaturing gel and visualized using a marker (radiolabel, fluorescent label or biotin) included in the reaction. The primers, preferably 9-mer oligonucleotides, are selected to be complementary to the most commonly used coding sequences in 200 mammalian genes, but having a low probability that two complementary sequences would appear in any individual mRNA. The cDNA patterns obtained represent a fingerprint of the mRNA which can be used to detect differential expression specific to an individual, a tissue, or the cell's physiological or differentiation state. The cDNA can be eluted and amplified and/or sequenced.

Various versions of DD-PCR methods have proved useful for comparing mRNA expression in closely related cell types or in a single cell type but differing in the physiological state of the cells (Liang, P. and Pardee, A. B., *Science* 257: 967–971, 1992; Zhao, S., Ooi, S. L. and Pardee, A. B., *Bio Techniques* 18: 842–850, 1995). These methods, however, have limited specificity in detecting mRNA species due to the procedures used. First, annealing primers at relatively low temperatures (e.g., 40° C.) compromises specificity and increases the likelihood of producing or encountering secondary structures in the template cDNA during amplification, thus producing an amplified cDNA population that is not truly representative of the expressed mRNA in the sample. Second, annealing degenerate primers or arbitrary primers at relatively low stringency results in incompletely defined specificity in the differential display (Zhao, S., Ooi, S. L. and Pardee, A. B., *Bio Techniques* 18: 842–850, 1995). Therefore, there is a need to increase the specificity of detection of mRNA species in a sample to allow more accurate detection of mRNA content that is characteristic of the cell, tissue or other samples. A method that produces a more specific differential display is useful for diagnosis of a physiological state of cells or tissue (e.g., diagnosis of tumor tissue or cancerous cells), identification of cells or tissue from a particular organ or individual and characterization of a cell's state of differentiation. A method that produces a more specific differential display is generally useful for medical or forensic applications that require characterization of a cell or tissue sample.

The present invention addresses the limitations of the previously known DD-PCR methods by using adaptor sequences that anneal to restriction enzyme recognition sites in the amplified cDNA. The method is called restriction display-polymerase chain reaction (RD-PCR).

SUMMARY OF THE INVENTION

According to the invention, there is provided a method for detecting and characterizing mRNA molecules including the steps of providing purified and isolated mRNA molecules, synthesizing a double stranded cDNA from the isolated mRNA, digesting the double stranded cDNA with a restriction endonuclease to produce cDNA fragments in which at least one end of the cDNA fragments has a sequence capable of hybridizing to an adaptor DNA sequence, wherein the improvement comprises hybridizing adaptor DNA sequences to at least one end of the cDNA fragments; ligating the adaptor DNA sequences to the cDNA fragments; amplifying the cDNA fragments having ligated adaptor DNA sequences by a polymerase chain reaction (PCR) using primer DNA sequences that hybridize to the ends of the cDNA fragments, wherein the primer DNA sequences have at least one nucleotide at the 3' end that specifically hybridizes to a subset of cDNA molecules; and detecting the presence of the resulting amplified cDNA fragments. In one embodiment, the method further comprises the step of cloning the amplified cDNA fragments in a vector using the adaptor DNA sequences to hybridize to complementary sequences in the vector. Another embodiment further comprises the step of sequencing the amplified cDNA fragments using primers including the adaptor DNA sequences to initiate DNA synthesis in a chain-terminating DNA sequencing reaction and identifying the sequences of the amplified cDNA fragments by comparing the sequences with known DNA sequences. In another embodiment, the amplifying step further comprises hybridizing the primer DNA sequences at a stringent hybridization temperature determined from the melting temperatures ($T_m$) of the primer sequences. In one embodiment of the method, the synthesizing step further comprises using a first primer DNA sequence, capable of hybridizing to said mRNA, wherein said first primer DNA sequence comprises, in a 5' to 3' orientation a 5'-adaptor DNA; one or more nucleotides adjacent to said 5'-adaptor DNA sequence; an oligo-dT sequence; and one or more nucleotides adjacent to said oligo-dT sequence, wherein the nucleotide directly adjacent to said oligo-dT sequence can be C, A or G but not T, and nucleotides proximal to the nucleotide directly adjacent to said oligo-dT sequence can be C, A, G or T, and wherein said nucleotides adjacent to said 5'-adaptor DNA sequence and adjacent to said oligo-dT sequence are capable of hybridizing to ribonucleotides occurring 5' of a poly-(A) sequence in mRNA molecules; and wherein said synthesizing step further comprises synthesizing a second strand of cDNA complementary to a first strand of cDNA made by using said first primer DNA sequence. One embodiment includes the amplifying step that further comprises using one primer DNA sequence comprising, in a 5' to 3' orientation, a DNA sequence complementary to said 5'-adaptor DNA sequence used in the synthesizing step, and at least one nucleotide capable of hybridizing to a subset of the cDNA molecules produced during the synthesizing step, and another primer DNA sequence comprising, in a 5' to 3' orientation, a sequence complementary to one strand of the ligated adaptor DNA sequences and at least one nucleotide capable of hybridizing to a subset of the cDNA molecules produced during the synthesizing step. Another embodiment includes the amplifying step which further comprises using primer DNA sequences comprising, in a 5' to 3' orientation, DNA sequences complementary to the ligated adaptor DNA sequences and at least one nucleotide capable of hybridizing to a subset of the cDNA molecules produced during the synthesis step. Yet another embodiment further comprises the steps of digesting amplified cDNA fragments with at least one restriction endonuclease capable of cutting the amplified cDNA sequences at a restriction endonuclease recognition site present in a primer DNA sequence and cloning the digested cDNA fragments into a vector. One embodiment further comprises synthesizing a cDNA from mRNA using a primer having the DNA sequence of SEG ID NO:2. In another embodiment, the hybridizing step further comprises using adaptor DNA sequences produced by hybridizing single stranded DNA molecules having the DNA sequences of SEQ ID NO:7 and SEQ ID NO:8. In one embodiment, the amplifying step further comprises using primer DNA sequences having the DNA sequences of SEQ ID NO:11 and SEQ ID NO:12. Preferably, the amplifying step further comprises using mixtures of primer DNA sequences varying at the 3' nucleotides, wherein the 3' nucleotides are selected from the group consisting of G, A, T or C for either or both of the primer DNA sequences. One embodiment of the method, further comprises digesting the cDNA with a restriction endonuclease that produces at least a one-nucleotide overhang at ends of the cDNA fragments after digestion is complete. In another embodiment, the amplifying step further comprises using primer DNA sequences having one, two or three nucleotides at the 3' end that specifically hybridize to a subset of cDNA molecules. Preferably, this embodiment further comprises using a mixture of primer DNA sequences, wherein the primer DNA sequences in the mixture vary at the one, two or three nucleotides at the 3' end. In one embodiment, the method includes the step of identifying the sequences of the amplified cDNA fragments by comparing the sequences with known DNA sequences. Preferably, the identifying step comprises comparing a DNA sequence of an amplified cDNA fragment with known DNA sequences, wherein the known DNA sequences contain a first restriction endonuclease recognition sequence adjacent to one or more nucleotides at the 3' end of the primer DNA sequences used in the amplifying step, and wherein the identifying step includes selecting known DNA sequences on the basis of DNA fragment size, wherein the size is determined by the distance between the first restriction endonuclease recognition sequence and a second restriction endonuclease recognition site and wherein the size of the known DNA sequence approximates the size of the amplified cDNA fragment. One embodiment further comprises a step of selecting for cDNA fragments containing a sequence complementary to a 3' end of mRNA.

Another aspect of the invention is a kit for characterizing cells or tissues based on the mRNA molecules contained therein, comprising at least one primer DNA sequence capable of hybridizing to the mRNA for synthesis of cDNA; adaptor DNA sequences capable of hybridizing to at least one end of cDNA fragments that have been cut with a restriction endonuclease; primer DNA sequences for use in a polymerase chain reaction to amplify the cDNA fragments, wherein the primer DNA sequences can hybridize to the ends of the cDNA fragments and have at least one nucleotide at the 3' end that specifically hybridizes to a subset of cDNA fragments; and buffers and enzymes for carrying out a polymerase chain reaction.

The accompanying drawings, which are incorporated in and constitute a part of the specification, illustrate various embodiments of the invention and, together with the description, serve to explain the principles of the invention.

DETAILED DESCRIPTION OF THE INVENTION

The essential steps of Restriction Display PCR are as follows: (i) synthesis of double stranded cDNA from purified mRNA; (ii) digestion of the cDNA with one or more restriction enzymes to produce cDNA fragments having one or two ends to which adaptor sequences can be hybridized and ligated; and (iii) PCR amplification of the cDNA fragments using sets of primers based on the adaptor sequences and adjacent bases. In this way, the cellular mRNA is divided into multiple portions (e.g., 196 portions) for identification of different subsets of the mRNA that are transcribed into cDNA, amplified and detected by any of a variety of well known methods. For example, the amplified DNA fragments may be separated on a polyacrylamide gel and visualized by eye or using an automated gel reader. Alternatively, the amplified fragments may be detected by using an automatic DNA sequencer which detects a label attached to the fragments. It will be understood that any known method of displaying and detecting the presence of DNA fragments that are representative of the expressed subset of genes in the sample is considered part of the method. Such methods include but are not limited to agarose or polyacrylamide gel separation and ethidium bromide staining of DNA fragments or autoradiography of DNA fragments radiolabeled with $^{35}S$, $^{32}p$ or $^{33}P$. Other well known methods of detection include detection of DNA fragments labeled with chemiluminescent compounds or by using an automated sequencing apparatus that detects fluorescent markers. Also included in known detection methods is detection of biotin-labeled compounds associated with the DNA using compounds that bind to biotin. Directly sequencing, or cloning and sequencing, the DNA fragments is another known method of characterizing the DNA fragments that are representative of the mRNA present in the sample.

Figure 1:
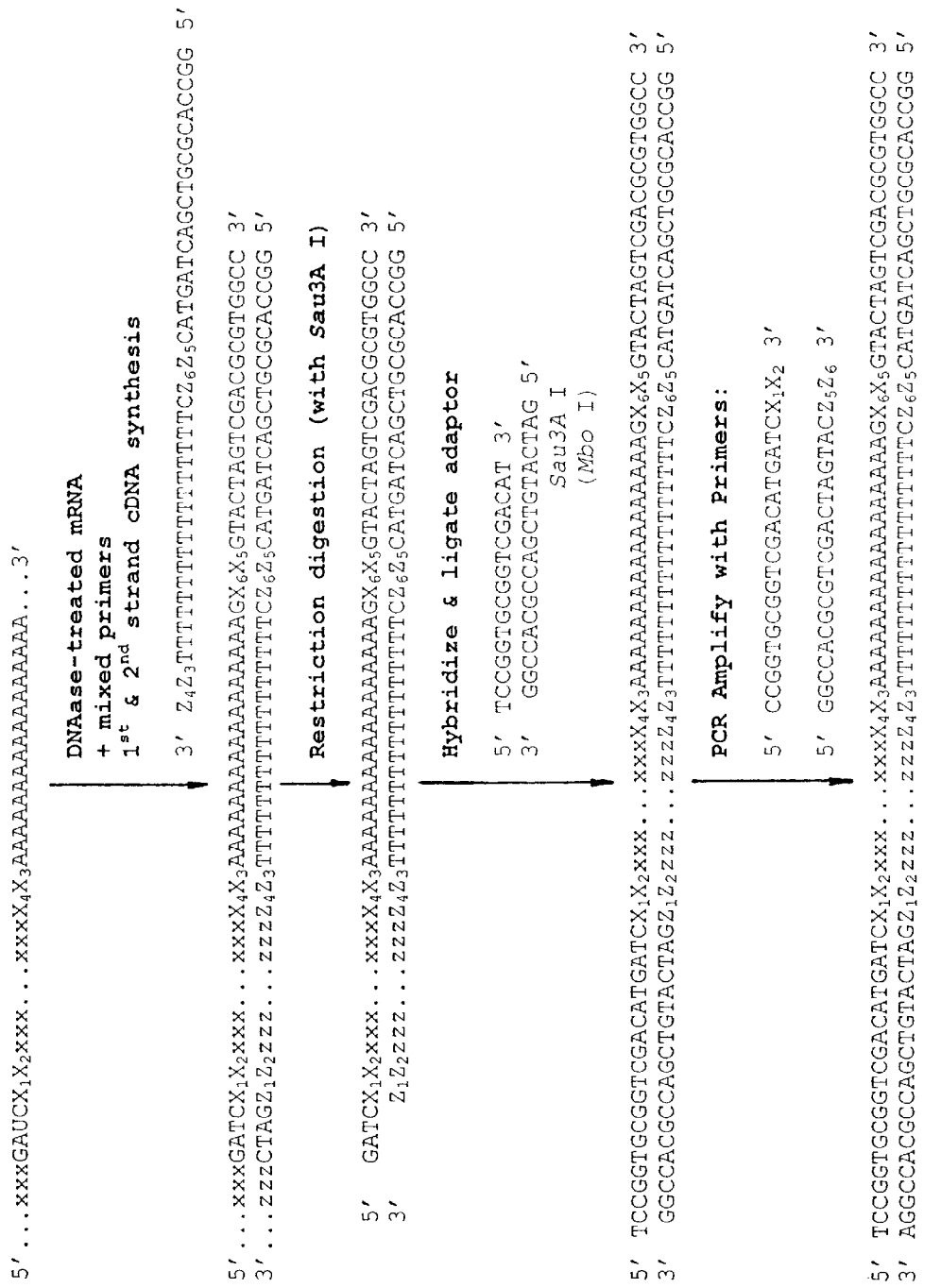
FIG. 1. Schematic diagram of one embodiment of RD-PCR, with specific primer and adaptor sequences shown. Nucleotides designated $X_1$, $X_2$, $X_4$, $X_5$ and $X_6$ can be any one of the four possible nucleotides (G, A, T or C), and $X_3$ and can be any one of G, T or C, but not A. Thus, the nucleotide pairs represented by $X_1X_2$ and $X_6X_5$ have 16 possible combinations, whereas the nucleotide pairs represented by $X_4X_3$ has 12 possible combinations. Generally, only 12 of the possible 16 combinations available for $X_6X_5$ would be used. The "Z" bases are the standard complementary bases that pair with the "X" base; "x" and "z" are bases of arbitrary sequence, with standard complementary base pairing in the cDNA. SEQ ID NO:1 SEQ ID NO:13 are illustrated in the figure and describe in the following text.

One embodiment of the method, diagrammed in FIG. 1, includes providing messenger RNA (mRNA) molecules, synthesis of complementary DNA (cDNA) fragments complementary in sequence to the sequence at the 3' ends of the cellular mRNA, and amplification of the cDNA fragments using PCR to produce identifiable DNA fragments. After amplification, the DNA fragments corresponding to the sequence at the 3' ends of the cellular mRNA are displayed and detected using any of a variety of well-known methods such as, for example, those discussed above. Another embodiment of the method, diagrammed in FIG. 2, uses similar procedures for restriction enzyme cutting and PCR amplification but allows for amplification and detection of portions corresponding to the entire length of mRNA, not just the 3' end.

Referring to FIG. 1, the method for amplification of sequences that occur at the 3' ends of mRNA utilizes the following steps. Exemplary sequences are shown in FIG. 1 for the sake of illustration. However, it will be understood that these sequences are only exemplary and are not intended to limit the invention to the use of the sequences shown. The method steps are indicated in bold letters in FIG. 1.

As shown in FIG. 1, the method begins with providing purified mRNA (e.g., DNAase-treated RNA containing poly-A sequences) from which a first strand of cDNA is synthesized using reverse transcriptase (RT) under standard conditions with anchored oligo-dT primers. Because the primers contain oligo-dT sequences which select for mRNA molecules, total RNA car be substituted for purified mRNA, as will be understood by those skilled in the art. An exemplary RNA strand is shown in the first line of FIG. 1 (5' . . . xxxGAUCX$_1$X$_2$xxx . . . xxxX$_4$X$_3$AAAAAAAAAAAAAAAAA3' (comprised of SEQ ID NO:1 at the 3' end and SEQ ID NO:3 at the 5' end except T is U)) and may vary in length as shown by the series of dots (" . . . "). The "x" bases represent random sequences of varying lengths as found in a population of RNA molecules. The mRNA sequence shown in FIG. 1 contains a poly-A tail at the 3' end, which may vary in sequence length (the 17-nucleotide poly-A tail is shown only for purposes of illustration). The mRNA sequence also contains a sequence 5' of the poly-A tail that, when made into a double-stranded cDNA will be recognized and cleaved by a restriction endonuclease, here shown as the GATC recognition site of the restriction endonuclease Sau3A I. The nucleotide positions occupied by X$_1$ and X$_2$ (adjacent to the 5' restriction endonuclease recognition sequence) and X$_4$ (located within one nucleotide of the 3' poly-A sequence) can be G, A, U or C; nucleotide position X$_3$ (located directly adjacent to the poly-A sequence) can be G, U or C. Thus, for the purposes of illustration, the important features of the mRNA shown in FIG. 1 are a sequence coding for a restriction endonuclease recognition site adjacent to nucleotides X$_1$ and X$_2$ (shown as GAUCX$_1$X$_2$) and nucleotides X$_4$ and X$_3$ adjacent to the 5' end of the 3' poly-A tail of the mRNA (shown as X$_4$X$_3$AAAAAAAAAAAAAAAAA (corresponding to SEQ ID NO:1)).

The mRNA sample is mixed with oligo-dT-containing primers, and first and second strand cDNA is synthesized using standard methods. The length of the oligo-dT portion of the primers may vary as is well known in the art, and preferably is from about 10 to 25 nucleotides in length. The oligo-dT containing primers also contain nested bases designated "Z$_4$Z$_3$" and "Z$_6$Z$_5$" near the 5' and 3' ends of the oligo-dT sequence. The poly-T containing primer shown in FIG. 1 is shown in the 3' to 5' orientation. The Z$_4$Z$_3$ nested bases are directly adjacent to the oligo-dT sequence at its 3' end, and the Z$_6$Z$_5$ nested bases are shown separated from the 5' end of the oligo-dT sequence by one base (called a "buffer base"). The buffer base shown in FIG. 1 is a C for illustration only and any base other than T could be used as the buffer base. Those skilled in the art will appreciate that the choice of buffer base may be used to influence the hybridization temperature used for the primer. Zero, one, two or three buffer bases may be used as desired.

The nucleotides Z$_4$ and Z$_3$ are complementary to nucleotides X$_4$ and X$_3$ in the mRNA. Therefore the Z$_4$ nucleotide can be G, A, T or C and Z$_3$ can be G, C or A, but the combination of Z$_4$ and Z$_3$ chosen for making the primer will determine the subset of mRNA that the primer will bind to (i.e., those mRNA that contain complementary X$_4$ and X$_3$ nucleotides). A primer having the features illustrated in FIG. 1 is SEQ ID NO:2 (in the 5' to 3' orie The Z$_6$ and Z$_5$ positions of the primer can be any nucleotide (G, A, T or C). The 5' portion of the primer includes any sequence of bases that can be used in cDNA synthesis and that subsequently can be used as hybridizing sequences for the primers used in PCR amplification (described in more detail below). Such sequences are represented, for example, by the 20 nucleotides at the 5' end of SEQ ID NO:2. It will be understood by those skilled in the art that other sequences and other lengths of sequences can be substituted for this portion of the sequence so long as the sequence is sufficiently long to hybridize to a primer for PCR amplification, preferably 10 to 30 nucleotides in length.

In choosing nucleotides for the Z$_4$Z$_3$ and Z$_6$Z$_5$ positions on the oligo-dT containing primer (and thus determining the complementary X$_4$X$_3$ and X$_6$X$_5$ positions found in the cDNA produced), one skilled in the art will realize that it is optimal to maintain a relatively constant GC:AT ratio in all the primer sequences so that the same experimental conditions can be used for all the first strand primers used (i.e., to equalize the melting temperature (T$_m$) for hybridization purposes for the different primers). Thus, for example, the choice of nucleotide for position Z$_3$ may affect the choice of the nucleotide for positions Z$_5$ and/or Z$_6$ to maintain the same GC:AT ratio for that primer as for other primers used. That is, if Z$_3$ is a C or G, then Z$_5$ or Z$_6$ would be A or T to balance the number of purine-pyrimidine bonds for purposes of maintaining approximately the same T$_m$ for this primer as for other primers used in the protocol. Similarly if Z$_3$ is A, then Z$_5$ or Z$_6$ would be G or C to maintain the GC:AT ratio. Those skilled in the art can readily determine the proper selection of nucleotides for these bases and can readily calculate the T$_m$ expected for any combination of bases using well known techniques (Sambrook, J., et al., *Molecular cloning. A Laboratory Manual.*, 2nd ed., vol. 1–3, Cold Spring Harbor Laboratory, Cold Spring Harbor, N.Y., 1989).

A cDNA second strand is synthesized using standard conditions with one or more arbitrary 3' primers (not shown in FIG. 1). Then, the double-stranded cDNA molecules are exhaustively digested with one or more restriction endonucleases that cut within the cDNA sequence to generate double stranded fragments capable of hybridizing to adaptor sequences. Preferably the restriction endonucleases produce one or more bases of overhang to facilitate hybridization of adaptor sequence. FIG. 1 shows a double-stranded cDNA sequence containing the arbitrary "x" and the complementary "z" nucleotides of varying lengths, indicated by the dots (" . . . "), as determined by the mRNA sequences in the sample. The important features of the double-stranded cDNA molecules are the restriction endonuclease site, here shown as that for restriction endonuclease Sau3A I (comprised of SEQ ID NO:3 and SEQ ID NO:4), and the double-stranded portions that include the poly-A and poly-T containing sequences (comprised of SEQ ID NO:5 and SEQ ID NO:6). As shown in FIG. 1, the restriction endonuclease Sau3A I will cut at any Sau3A I restriction endonuclease recognition sites found in the entire cDNA sequence. FIG. 1 shows only the restriction endonuclease recognition site closest to the end of the cDNA corresponding to the 3' end of the mRNA used to synthesize the double-stranded cDNA (comprised of SEQ ID NO:3, SEQ ID NO:4, SEQ ID NO:5 and SEQ ID NO:6 with bases between shown by the "x" and "z" nucleotide positions and the dots, as described above). After restriction cutting, the DNA fragment is comprised of SEQ ID NO:3, the $Z_1$ and $Z_2$ nucleotides, SEQ ID NO:5 and SEQ ID NO:6 with bases between shown by the "x" and "z" nucleotide positions and dots, as described above. Although Sau3A I is shown in FIG. 1, any restriction endonuclease that cuts DNA using standard methods is envisioned as useful in the method, including for example all known restriction nucleases that recognize sites consisting of 4 to 6 nucleotides.

Adaptor sequences (shown in FIG. 1 as a double-stranded DNA fragment comprised of SEQ ID NO:7 and SEQ ID NO:8) containing one or more restriction endonuclease recognition sites and capable of hybridizing to the cut ends of the cDNA fragments are then hybridized and ligated to the cDNA fragments. FIG. 1 shows an adaptor sequence containing a Sal I restriction endonuclease recognition site (GTCGAC) and having an overhang end corresponding to the Sau3A I cut site and capable of hybridizing to the Sau3A I ends of the cDNA fragments. In FIG. 1, the adaptor sequence hybridizes only to one end of the fragment which was cut with Sau3A I because the other end contains the oligo-d(A/T) sequence of the cDNA. After hybridization and ligation of the adaptor, the resulting double-stranded DNA fragment shown in FIG. 1 is comprised of SEQ ID NO:5 and SEQ ID NO:6 at the end containing the oligo-d(A/T) sequences and SEQ ID NO:9 and SEQ ID NO:10 at the end containing the ligated adaptor sequences, with lengths of "x" and "z" nucleotides indicated by the dots, as described above.

The adaptor sequences can ligate to fragments that contain a poly-A/poly-T containing double-stranded end and only a single opposite end that specifically hybridizes with the adaptor overhang sequence (as shown in FIG. 1) as well as to cDNA fragments that have two ends that specifically hybridize with the adaptor overhang sequence (i.e., internal digestion fragments that do not contain the poly-A/poly-T sequences). Therefore, to make this embodiment specific for detecting molecules that represent the 3' ends of the mRNA in the sample, an additional step can be included to specifically select for or detect the molecules containing a strand complementary to the 3' ends of the mRNA. For example, before the PCR amplification step, a hybridization selection dependent on binding to an oligo-dA and/or oligo-dT probe could be included in the method. Such methods are well known in the art and could include, for example, melting the double-stranded molecules with attached adaptors and selecting oligo-dA containing sequences by passing the melted strands over a solid support having attached oligo-dT fragments, and then eluting the captured DNA strands for PCR amplification.

Another modification that may be incorporated into the method is to use adaptor molecules in which only the long arm of the double-stranded adaptor is phosphorylated. Only phosphorylated strand then can be ligated to the cDNA molecules. After ligation of the adaptors, the short arm single strands of the adaptors can be melted away by adjusting the temperature to above the $T_m$ of the adaptor molecules. Then amplification using the PCR primers proceeds as described herein.

PCR amplification of the cDNA fragments is done under standard conditions using primers (1) containing sequences used for the first strand cDNA synthesis and (2) capable of priming from the adaptor fragment sequence. Two such primers are shown in FIG. 1 (SEQ ID NO:11 and SEQ ID NO:12). The "$X_1X_2$" positions in the primer can be any combination of G, A, T or C, resulting in 16 possible combinations. Similarly, the $Z_5$ and $Z_6$ positions in the second primer can be any combination of G, A, T or C resulting in 16 possible combinations. Preferably, the "$Z_5$" position in the second primer is any nucleotide (G, A, T or C), whereas the "$Z_6$" position is any nucleotide except T, thus providing for 12 possible combinations of $Z_5$ and $Z_6$ in the mixed primers. The primer sequences can be random sequences, can be arbitrarily determined sequences, or can be sequences designed, for example, to avoid hairpin turns, self-hybridization and/or hybridization to known gene sequences, as will readily be determined by those skilled in the art. The primer sequences may contain an oligo-dT portion for priming poly-A containing DNA fragments. The primer sequences may also include any known restriction endonuclease recognition sequence for subsequent use in cloning the amplified DNA fragments into a vector containing the appropriate restriction endonuclease site, after restriction endonuclease digestion of the amplified DNA fragments.

All possible combinations of primers can be used in separate reactions. Alternatively, combinations of primers having known sequences at the $X_1X_2$ and $Z_5Z_6$ positions can be used to reduce the total number of reactions performed to generate a RD-PCR fingerprint. The cDNA fragments with adaptor end(s) are amplified by PCR using primers with sequences corresponding to the primer used in first strand cDNA synthesis (with or without the oligo-dT portion) and the adaptor sequence. For example, SEQ ID NO:2 could be used as a primer in the PCR.

The 3' base chosen for the primer (e.g., $X_2$ and $Z_6$ in FIG. 1) is the base most important for determining specificity during PCR amplification. The PCR amplification can be modified by using different sets of primers during early cycles of amplification than are used in the later amplification cycles to protect against the small percentage of amplification errors that occur due to inappropriate hybridization of primers. That is during the first ten to twenty-five cycles of amplification, one set of primers containing a specific 3' base may be used. This will ensure the first selection step during amplification. Then, during subsequent amplification cycles, another set of primers can be used in which the 3' base and the penultimate base ($X_1X_2$ and $Z_5Z_6$ in FIG. 1) are specifically chosen to amplify fragments produced during the first amplification cycles, but lending more specificity to the amplification by virtue of the combination of the 3' base and the penultimate base. This can be accomplished in a variety of ways which can easily be determined by those skilled in the art. For example, the first ten cycles of amplification can use four aliquots of total cDNA, with one primer for each of the possible 3' bases added to the aliquots for amplification (i.e., tube 1 receives a 3'-A primer, tube 2 receives a 3'-G primer, etc). After the first 10 to 25 cycles of amplification are completed, these four tubes can be each split into four more aliquots into which an excess of the second set of primers is added for the later cycles of amplification (e.g., tube 1 is split into tubes 1.1, 1.2, 1.3 and 1.4, and then 3'-AA primer is added to tube 1.1., 3'-AT is added to tube 1.2, 3'-AC primer is added to tube 1.3, and 3'-AG is added to tube 1.4, and so on for all the remaining aliquots for a total of 16 tubes per beginning cDNA sample). Alternatively, 16 tubes may be started during the first amplification cycles (four groups of four), and the second set of primers is added in excess appropriately to the sixteen tubes after 10 to 25 cycles, thus eliminating the need to make aliquots in the middle of amplification. This sequential amplification modification adds more specificity to the cDNA that are amplified for detection using any of the known detection methods available. This eliminates some of the mispriming during amplification which is typical of differential display methods.

The PCR amplified fragments are then analyzed by separation and visualization (e.g. on an agarose or polyacrylamide gel and using staining or autoradiography of the DNA fragments), by DNA sequencing or by direct cloning into a vector for later DNA sequencing. All of these techniques of detecting DNA fragments use molecular genetic techniques well known to those skilled in the art (Sambrook, J., et al., *Molecular cloning. A Laboratory Manual.*, 2nd ed., vol. 1–3, Cold Spring Harbor Laboratory, Cold Spring Harbor, N.Y., 1989). In FIG. 1, the PCR-amplified DNA is shown as a double-stranded DNA fragment comprised of SEQ ID NO:9 and SEQ ID NO:13 at the end corresponding to the end to which adaptor sequences were ligated before amplification, and SEQ ID NO:5 and SEQ ID NO:6 at the poly(dA)/poly (dT) double-stranded end, with the two ends connected by the sequence indicated by the "x", "z" and dots representing nucleotide positions, as described earlier.

The adaptor sequences can ligate to fragments that contain a poly-dA/poly-dT double-stranded end (corresponding to the 3' end of the mRNA) and a single opposite end that specifically hybridizes with the adaptor overhang sequence (as shown in FIG. 1). The adaptor sequences can also ligate to cDNA fragments that have two ends that specifically hybridize with the adaptor overhang sequence (i.e., internal restriction digest fragments that do not contain the poly-dA/ poly-dT sequences. Therefore, the detecting step can be modified to make it specific for DNA molecules that represent only the 3' ends of the mRNA molecules in the sample. The amplified cDNA molecules that contain a strand complementary to the 3' end of the mRNA molecules can be detected in other known ways such as by including a label (e.g., radioactive or fluorescent) attached to the PCR primer that contains the $Z_6Z_5$ nucleotides (e.g., SEQ ID NO:12 for the example shown in FIG. 1). Then, the fragments amplified by the labeled primers are detected after amplification by detecting the primer label, using well known methods, and thus detecting only those molecules that represent the 3' ends of the mRNA in the sample. Similarly, the detection step can include a hybridization probe that specifically binds to sequences that are contained in the DNA fragments made from the 3' ends of the mRNA. For example, the entire population of amplified molecules could be hybridized (e.g., using Southern blotting) with a probe specific for the 3' sequences to detect the molecules that represent the 3' ends of the mRNA in the sample. Such specific probes can include an oligo-dA sequence, an oligo-dT sequence and/or the 3' adaptor sequence.

Direct cloning is accomplished by exhaustively digesting the amplified cDNA with a restriction endonuclease (e.g. Sau3A I as in FIG. 1) to cut at restriction endonuclease recognition sites present in the cDNA sequences or supplied by the primer and adaptor sequences. The cut sites at the ends of the DNA fragments are used to clone the DNA into an appropriately cut vector.

Figure 2:
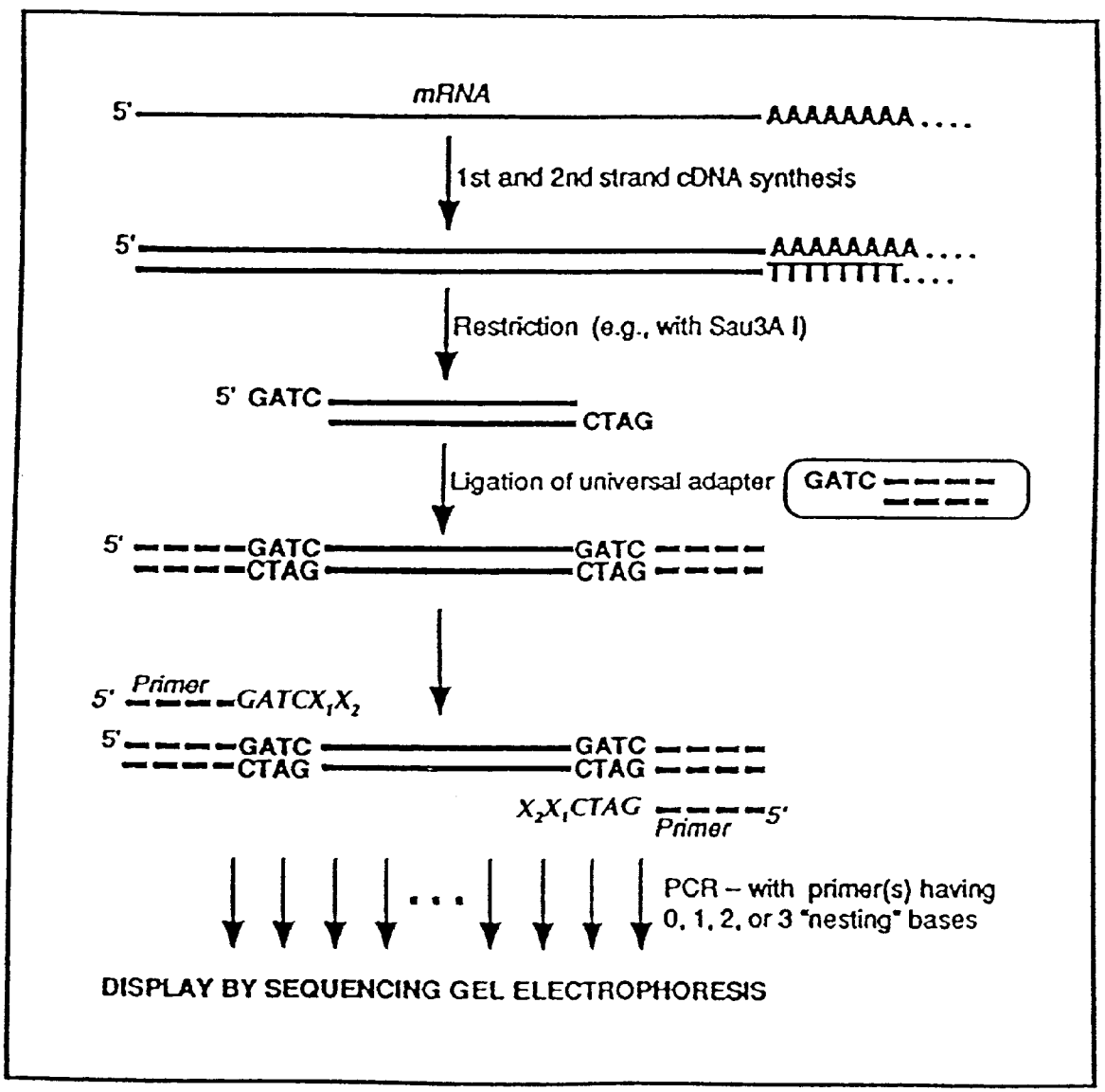
FIG. 2. Schematic diagram of one embodiment of RD-PCR using primers having two 3'-nesting bases (represented by "$X_1X_2$") and capable of amplifying fragments within an entire mRNA sequence.

Another embodiment of the basic RD-PCR protocol that allows for amplification of all cDNA corresponding to the entire length of mRNA, not just the 3' end, is shown schematically in FIG. 2. As in the embodiment of the method shown in FIG. 1, for amplifying fragments corresponding to the 3' end of mRNA, this embodiment begins with synthesis of double-stranded cDNA from purified mRNA using methods well known to those skilled in the art. The cDNA is then restricted with a restriction endonuclease (e.g., Sau3A I) to produce fragments with two cohesive ends resulting from cutting at the restriction endonuclease recognition sites. It will be understood that fragments at the ends of the cDNA will have only one cohesive end, with the other noncohesive end representing the 5' or 3' end of the mRNA transcript. Universal adaptors with one cohesive end capable of hybridizing to the ends of the restriction endonuclease-cut cDNA fragments are ligated to the fragments at the cut sites, and excess adaptors are removed using standard methods. Next, PCR is performed with primers that are identical to the universal adaptor (i.e., containing the restriction site sequence) but also including one, two, or three specific "nesting" bases (two are shown in FIG. 2 as $X_1$ and $X_2$) at the 3' end. These nesting bases add specificity to the differential display produced because they hybridize to a selected subset of the cDNA produced. The PCR reactions can be performed for the various single primers (i.e., one set of $X_1X_2$-containing primers) or combinations of primers (i.e., primers having different combinations of bases at the $X_1X_2$ positions), and the products are analyzed using any of a variety of methods well known to those skilled in the art (e.g., displayed on a gel). By using single primers or combinations with different 3'-nesting bases, it is possible to control the number of bands, within broad limits, that appear for each PCR amplification reaction mixture. Because the specificity of PCR amplification is controlled by the primers selected, cells can be characterized by the specific fingerprint that is generated for a particular source of mRNA and the primers used for amplification.

It will be understood by those skilled in the art that a combination of two different restriction endonucleases may be used to generate cDNA fragments that are capable of insertion in a directional manner into an appropriately cut vector utilizing asymmetrical restriction sites on the ends of the fragments. This could be achieved by placing two different restriction endonuclease recognition sites in the adaptor sequence (e.g., Sal I and Sau3A I or Sal I and Not I recognition sites). The presence of restriction sites at each end of the amplified fragments provides for efficient cloning of DNA fragments corresponding to the 3' sequences of differentially expressed mRNA.

Clones produced by this method are useful as probes (e.g., for assaying mRNA content of cells from additional sources or for screening DNA libraries) and/or for DNA sequencing, allowing more precise characterization of the cells based on their expressed genes. For example, the sequences of the clones may be compared to databases of known DNA sequences to precisely identify the expressed gene or related gene(s). In one such computer-aided comparison, the DNA sequences of an existing database are segmented into subsets based on the restriction endonuclease recognition sequences in combination with the nesting bases that are used in a particular RD-PCR reaction (e.g., the computer software separates into one subset all DNA sequences in the data base that are terminated by a Sau3A I restriction site adjacent to the bases shown as $X_1X_2$ in FIG. 1). From that subset of DNA sequences in the database, the computer then selects DNA sequences that correspond approximately in size to those identified by the display of the RD-PCR products (e.g., if fragments of about 150 bp were visualized from the RD-PCR display, the computer would select sequences in the database subset that have about 150 bases between Sau3A I sites and adjacent nesting bases to the 3' ends. From the smaller subset of potential matches to known sequences (if ambiguity remained), the skilled artisan would further establish the identity of the RD-PCR products by techniques well known in the art (e.g., direct sequence comparison, DNA hybridization with a probe of known sequence and the like). By modifying the searching parameters the skilled artisan could identify related but not identical DNA sequences (i.e., a member of a family of gene sequences) with those amplified using the RD-PCR method.

DNA sequences obtained using the embodiment shown in FIG. 2 can be readily compared to DNA sequences in data banks to identify the expressed genes. Because essentially all of the mRNA expressed in the cell will be amplified by this embodiment (possibly in multiple reactions, depending on the primers used), the DNA sequences obtained have a high probability of revealing regions which may have already been identified and may be available by comparison to a DNA data bank. Thus, the DNA sequences will provide a specific characterization of genes expressed in the cells or tissue from which the mRNA was obtained.

Commercially available primers for cDNA synthesis may be used in the method and the same adaptors may be used for both the 3' and 5' ends, making the procedure somewhat simpler to perform. Alternatively, specifically designed primers (e.g., with specific nesting bases and/or sequences specific for a known gene or gene family or a predicted DNA sequence) can be synthesized using methods well known to those skilled in the art. Because most of the primer sequences used include a majority of the same sequences (i.e., those contributed by the adaptor sequence), the same PCR conditions can be used for all the combinations of primers, thus simplifying the procedure. This aspect is particularly useful for using the method in a kit for diagnostic characterization of cells where the user of the kit may have limited facilities for varying incubation temperatures.

The primers chosen for PCR amplification result in specificity of the mRNA fragments that are amplified and detected. In some cases, the combination of primer sequences and the size of the fragments amplified is sufficient to identify the presence of a particular species of mRNA in the cells being tested. Primers specifically designed to detect expression of a known gene or gene family lend further precision to the method for detecting the presence of a particular mRNA species. In particular, the identity of a fragment obtained with one primer (or set of primers) can be confirmed by predicting and finding a second fragment from the mRNA transcript using a second primer (or second set of primers).

The RD-PCR method is flexible and has several attractive features for characterization of differential gene expression, especially for optimization of the characterization of particular cells. The protocol can be optimized for a particular restriction endonuclease and adaptor sequence pair. Moreover, mixing and matching of different combinations of restriction endonuclease recognition sites used in cutting the cDNA and adaptor sequences added to the cDNA fragments increases flexibility of the method, particularly for cloning into selected vectors. A universal adaptor can be designed with considerable latitude, e.g., to minimize complementarity to sequences in genomic DNA and incorporate useful restriction sites or other motifs known to be expressed or of particular interest for selection of clones. Thus, the specificity of selection of amplified cDNA is well-defined by the restriction sites and 3'-nesting bases of the primers. Furthermore, adaptors and primers can be designed for hybridization at relatively high $T_m$ to minimize or eliminate competing hybridizations and mRNA secondary structure. The primers used in a particular set are optimally designed for compatibility in $T_m$, because they differ only in the 3'-nesting base(s).

The invention can be better understood by way of the following examples, which are representative of the preferred embodiments of the invention. Unless otherwise defined, all scientific and technical terms used herein have the same meaning as commonly understood by those skilled in the art. Unless stated otherwise, the techniques employed herein are standard methodologies well known to those skilled in the art.

EXAMPLE 1

Restriction Display-PCR Methodology

The following example presents the sequence of individual steps used in the basic RD-PCR method. It will be understood by those skilled in the art that variations of this basic method (e.g., varying the primers used in first strand cDNA synthesis) are possible while practicing the RD-PCR method. Such variations are contemplated and are well known to those with ordinary skill in the art.

Cells are harvested into a detergent buffer, and mRNA is prepared from the lysate by standard methods well known to those skilled in the art (e.g., Sambrook, J., et al., *Molecular cloning. A Laboratory Manual.*, 2nd ed., vol. 1–3, Cold Spring Harbor Laboratory, Cold Spring Harbor, N.Y., 1989). Contaminating DNA is eliminated by treatment with RNase-free DNAse.

First strand cDNA is synthesized using a primer that includes (from 5' to 3' of the primer): an adaptor that includes a two-base sequence near the junction with the oligo-dT region designated $4Z_6$, in which both $Z_5$ and $Z_6$ can be C, A, G or T, a buffer base, an oligo-dT sequence, and two bases designated $Z_3Z_4$, in which $Z_3$ can be C, A or G but not T, and $Z_4$ can be C, A, G or T. The 5' and 3' pairs of bases, $Z_5Z_6$ and $Z_3Z_4$, respectively, may be identical to each other or may be different.

The primer for first strand cDNA synthesis may also include a restriction endonuclease recognition sequence (e.g., a rare cutter restriction endonuclease recognition sequence such as that of Sal I enzyme) for later use in cloning. An example of such a primer is:

(SEQ ID NO:14)
5'GGCCACGCGTCGACTAGTAC$Z_5Z_8$CTTTTTTTTTTTTTTTTT$Z_3Z_4$ 3'.

Primers including all twelve possible pairs of 5' $Z_3Z_4$ (as described above) are used, either singly or combined into a primer mixture. Two of the twelve possibilities are:

5' GGCCACGCGTCGACTAGTACZ$_5$Z$_8$CTTTTTTTTTTTTTTTTCG 3', (SEQ ID NO:15)

and

5' GGCCACGCGTCGACTAGTACZ$_5$Z$_6$CTTTTTTTTTTTTTTTTGC 3'. (SEQ ID NO:16)

Preferably, the $Z_3Z_4$ and $Z_5Z_6$ bases are selected to balance the AT/GC ratio to allow for efficient hybridization of primers in the subsequent PCR amplifications, especially so that the same hybridization conditions can be used for all PCR reactions. Those skilled in the art will recognize that a preferred combination of $Z_3Z_4$ and $Z_5Z_6$ bases are selected to preserve the balance of base pairing and maintain an optimal hybridization temperature of the primer sequences. For example, if $Z_3Z_4$ are GC or CG, then $Z_5Z_6$ are preferably AT or TA.

It will be understood that in the complementary strand to each of the primers, nucleotides complementary to the Z nucleotides (designated "X" in FIG. 1) will be present according to standard base pairing. That is, if Z is A, then the corresponding complementary X base is T on the newly synthesized strand.

In a simpler version of the RD-PCR method, first strand cDNA synthesis is primed using any standard oligo-dT containing primer (many of which are commercially available) even those without an adaptor sequence. When such primers are used for first strand cDNA synthesis, anchored oligo-dT containing primers containing a restriction endonuclease recognition sequence are used in the subsequent PCR amplifications to add an appropriate recognition sequence to the ends of the amplified cDNA fragments.

Following first strand cDNA synthesis, second strand cDNA is synthesized by standard methods well known to those skilled in the art (e.g., as in Sambrook, J., et al., *Molecular cloning. A Laboratory Manual.*, 2nd ed., 1989).

The double stranded cDNA reaction mixture is treated to eliminate excess primer and other low molecular weight species and recover the cDNA. Any of a variety of well known methods including DNA precipitation or filtration through a gel matrix can be used (Sambrook, J., et al., *Molecular cloning. A Laboratory Manual.*, 2nd ed., 1989).

The double stranded cDNA is then exhaustively digested with an appropriate restriction endonuclease using appropriate salt and temperature conditions to cleave the primers and generate an overhang for hybridization of an adaptor DNA fragment. For example, the restriction endonuclease used in the method shown in FIG. 1 is Sau3A I, which recognizes GATC and produces a 5' GATC overhang. A restriction endonuclease that recognizes a four base pair sequence is preferred. Theoretically, such a restriction endonuclease will produce cDNA oligonucleotides averaging about $4^4=256$ bases beyond the oligo-dT tail. After enzymatic digestion is completed, the restriction endonuclease is inactivated by any of a variety of known procedures (e.g., by heating the mixture or chemically extracting the protein).

It will be appreciated by those skilled in the art that a mixture of restriction endonucleases that recognize larger restriction endonuclease recognition sequences (e.g., six-nucleotide sequences such as recognized by restriction endonucleases EcoR I and BamH I) may be used in place of a restriction endonuclease that recognizes a four base pair sequence. The combination of two (or more) restriction endonucleases can be used to generate fragments of a predicted size based on the frequency of cutting in cDNA of the species for which the method is being used. Such average restriction fragment size predictions can be readily calculated by those skilled in the art.

An adaptor DNA sequence that includes the overhang produced by the restriction endonuclease digestion is added in excess, hybridized to the cDNA fragments under appropriate conditions and ligated to the cDNA using methods well known in the art. The adaptor sequence may include an appropriate additional restriction endonuclease recognition sequence for a relatively rare-cutter enzyme (e.g., the Sal I recognition sequence of GTCGAC) for later use in cloning the cDNA fragments.

An example of a Sal I-containing adaptor is the double stranded DNA fragment made up of the two single strands of DNA: 5' TCCGGTGCGGTCGACAT 3' (SEQ ID NO:7) and 5' GATCATGTCGACCGCACCGG 3' (SEQ ID NO:8). When hybridized, these two strands form the double-stranded adaptor:

5' TCCGGTGCGGTCGACAT (SEQ ID NO:7)

GGCCACGCCAGCTGTACTAG 5' (SEQ ID NO:8)

as shown in FIG. 1.

The 5' GATC overhang of the adaptor hybridizes to the overhang produced when the cDNA is cut with Sau3A I.

PCR is performed using one primer corresponding to the 3' adaptor sequence plus two bases designated $X_1X_2$ in FIG. 1. The two bases shown as $X_1X_2$ in FIG. 1 can be C, A, G or T, in any of sixteen possible combinations. The two bases $X_1X_2$ are used to select a particular cDNA subpopulation from the entire population of cDNA produced in the earlier steps.

Sample primers appropriate for synthesis of the "sense" strand of the cDNA molecules as shown in FIG. 1 are:

5' CCGGTGCGGTCGACATGATCX$_1$X$_2$ 3' (SEQ ID NO:11)

in which $X_1X_2$ represent either G, A, C or T. Thus two of the sixteen possible primer oligomers are:

5' CCGGTGCGGTCGACATGATCGC 3' (SEQ ID NO:17)

and

5' CCGGTGCGGTCGACATGATCCG 3'. (SEQ ID NO:18)

These primers include sequences present in the 5' adaptor (i.e., present in SEQ ID NO:7) and illustrated in FIG. 1. The primers represented by SEQ ID NO:17 and SEQ ID NO:18 are each 22 nucleotides long, containing nucleotides for fifteen GC base pairings and seven AT base pairings when hybridized to a complementary sequence.

A sample primer appropriate for synthesis of the "antisense" strand of the cDNA molecules is:

5' GGCCACGCGTCGACTAGTACZ$_5$Z$_6$ 3' (SEQ ID NO:19)

in which $Z_5$ represents G, A or C and $Z_6$ represents either G, A, C or T.

Two of the twelve possible oligomers represented by SEQ ID NO:19 are:

```
5' GGCCACGCGTCGACTAGTACCG 3'      (SEQ ID NO:20)

and

I
5' GGCCACGCGTCGACTAGTACGC 3'.     (SEQ ID NO:21)
```

The primers represented by SEQ ID NO:20 and SEG ID NO:21 are each 22 nucleotides long containing nucleotides for fifteen GC base pairings and seven AT base pairings when hybridized to a complementary sequence.

Separate PCR reactions are run for each combination of primers, or mixtures of primers are used in individual PCR amplifications. There are twelve possible anti-sense primers (3×4) for hybridization to the cDNA representing the original 3' end of the mRNA, and sixteen possible sense primers (4×4) for the end of the cDNA representing a sequence internal to the original mRNA. If each possible combination of primers is run as a separate reaction, a total of 196 PCR samples would be produced and analyzed. Alternatively, to reduce the number of reactions to be analyzed for any population of cDNA molecules, the primers can be mixed or synthesized as a mixture in which degeneracy is introduced at the positions of the random bases.

Any standard method well known to those skilled in the art can be used to label the PCR products with a fluorescent, radioactive or chemical marker for subsequent detection. Similarly, any standard method of separation including electrophoretic separation of fragments on a DNA sequencing polyacrylamide gel or separation by analysis of fragments with an automated sequencing machine may be used to analyze the RD-PCR fingerprint produced.

If desired, the additional restriction sites (e.g., Sal I and Not I) present at the ends of the amplified cDNA fragments by means of the attached adaptor and/or primer sequences can be used for cloning and sequencing of cDNA in the individual bands detected.

EXAMPLE 2

Optimization of Conditions for Adaptor Addition

For rational optimization of the RD-PCR protocol, a test system having a sufficiently simple pattern of fragments in the appropriate molecular weight range was used to test for false positives and negatives at various intermediate stages in the procedure. The plasmid pBR322, which is 4,361 base pairs long, was used with a restriction endonuclease Sau3A I, which recognizes GATC and produces a 5'-GATC overhang. There are 22 Sau3A I restriction endonuclease recognition sites in pBR322 DNA. Some Sau3A I recognition sites were too close together to permit effective amplification and detection of the DNA fragments.

The Sau3A I fragments of pBR322 cDNA present in the restriction endonuclease reaction mixture were compared before and after ligation with an excess of the RD-PCR universal adaptor. Fragments were visually observed following electrophoretic separation of the fragments on an agarose gel using standard methods of gel separation and visualization of the DNA fragments following ethidium bromide staining.

The RD-PCR universal adaptor was formed by mixing two single-stranded oligonucleotides: 5' GATCCACAC-CAGCCAAACCCA 3' (SEQ ID NO:22) and 5' GGTTTG-GCTGGTGTG 3' (SEQ ID NO:23) to final concentrations of 500 and 600 μg/ml, respectively, in 10 mM Tris-HCl (pH 7.6), 5 mM MgCl$_2$ at 90° C. It will be understood by those skilled in the art that the strand of DNA represented by SEQ ID NO:22 has a phosphate at the 5' end to allow ligation to the Sau3A I cut end of the cDNA fragments. After 5 minutes the adaptor solution was slowly cooled to room temperature over a period of 30 minutes and subsequently stored at −20° C. between uses. The resulting heteroduplex adaptor as shown below:

```
5' GATCCACACCAGCCAAACCCA 3' (SEQ ID NO:22)

3'     GTGTGGTCGGTTTGG 5' (SEQ ID NO:23)
``` had a 5' overhang (GATC) for ligation to the mRNA restriction fragments and a two-base 3'-overhang (CA) at the opposite end to prevent blunt end self-ligation.

One μg of pBR322 circular DNA was digested for 2 hrs at 37° C. with 10 units of Sau3A I (Promega) in 20 μl of the buffer containing 25 mM Tris-Acetate, pH 7.8 (at 25° C.), 100 mM K-acetate, 10 mM Mg-acete, 1 mM DTT (or an equivalent buffer as recommended by the supplier of the restriction endonuclease), purified through a size separation matrix (an S-400 spin column obtained from Pharmacia), and ligated with 50-fold molar excess of universal adaptor for 15 min. at 37° C. A similarly digested aliquot of pBR322 DNA to which no adaptor DNA had been ligated was used for comparison, and both samples were separated by electrophoresis in separate lanes of an agarose gel as described above using a 100 base pair ladder (obtained from GIBCO/BRL) as molecular weight standards in an adjacent lane.

The fragments obtained after complete digestion, before and after ligation of the universal adaptor, were visualized by staining the gel with ethidium bromide and photographing it under ultraviolet light using standard procedures. After ligation of the universal primer, each pBR322 fragment migrated at an apparent molecular weight consistent with the increase of approximately 36 base pairs compared to that of the unligated control fragments, as expected for addition of an adaptor at each end. Because the plasmid is circular, all fragments have Sau3A I sites at each end and therefore all were expected to have two adaptors per fragment.

No fragments representing incomplete restriction or ligation were seen. An intensely stained spot at low molecular weight (of less than about 100 base pairs) was seen only in the experimental lane and presumably represented dimers of adaptors.

EXAMPLE 3

Detection of Differentiation in a Human Erythroleukemia Cell Line Using RD-PCR

The RD-PCR method was used to analyze the mRNA content of the cell line K562, a human erythroleukemia line that expresses the translocation product bcr-abl. The protocol diagrammed in FIG. 2 and discussed above was used. The aim was to assess changes in erythroid-specific mRNA expression when the cells were stimulated to differentiate by hemin, the iron-containing form of protoporphyrin IX. Hemin has been reported to stimulate the transcriptional regulatory activity of enhancer elements containing binding sites for the transcription factor NF-E2 (Palma, J. F., Gao, X., Lin, C., Wu, S. and Solomon, W. B., *Blood* 84: 1288–1297, 1994).

The mRNA was obtained from the erythroleukemia cell line K562 and hemin-stimulated K562 cells, and the RD-PCR procedure was performed in duplicate for each mRNA sample. The samples were separated on a gel in triplicate lanes for each assay, and the RD-PCR results were visualized by autoradiography. PCR primers used for DNA amplification contained nesting bases (the $X_1X_2$ and $Z_5Z_6$ nucleotides of FIG. 2) that were either "AA" or "AT". That is, both primers contained "AA" nesting bases (designated AA/AA), or both primers contained "AT" nesting bases (designated AT/AT), with the remainder of the primer sequence being identical for both the AA and AT types of primers. Size marker DNA fragments were run on a separate lane of the same gel for determination of the sizes of the amplified DNA fragments.

Poly-A containing RNA was purified using standard methods of hybridization to, and elution from, oligo-dT cellulose (using the QuickPrep Micro mRNA purification kit obtained from Pharmacia), and RNase-free DNase I was used to remove any residual DNA. Any of a variety of methods well known to those skilled in the art for obtaining DNA-free mRNA could be used. Purified mRNA was reverse-transcribed to double-stranded cDNA using standard conditions with an oligo-dT containing primer (e.g., as provided in the TimeSaver cDNA synthesis kit purchased from Pharmacia).

Given the expected number of transcripts in a cell, a primer complementary to the universal adaptor without the 3' nesting bases would be expected to produce a smear of PCR amplification products on the gel when PCR was performed. A smear of fragments of about 100–600 base pairs (bp) was typically observed on the gel when such a primer was used.

In contrast, the RD-PCR products obtained with primers that had two 3'-nesting bases, which would be expected to amplify only $\frac{1}{4}^{2+2}=\frac{1}{256}$ of the fragments, produced about 35–60 bands ranging in size from 200 base pairs to about 600 base pairs.

One $\mu$g of each cDNA was restricted with Sau3A I and ligated with the universal adaptor essentially as described in Example 2.

The PCR primers, 5' GTTTGGCTGGTGTGGATCAA 3' (SEQ ID NO:24) and 5' GTTTGGCTGGTGTGGATCAT 3' (SEQ ID NO:25), were based on the universal primer as described above but included two 3'-nesting bases (AA or AT).

All PCR reactions were done in a final volume of 50 $\mu$l containing 1–100 ng of cDNA, 25 pmol of each primer, 2.5 units of Taql DNA polymerase, 50 mM KCl, 10 mM Tris-HCl (pH 8.8), 1.5 mM $MgCl_2$, 0.1% Triton X-100, 200 $\mu$M each of dGTP, dCTP and dTTP and 75 $\mu$M of dATP and trace amounts of [$\alpha^{33}$P]-ATP for labeling. Typically, amplification was for 30 cycles, each consisting of 1 min at 92° C., 1 min at 56° C. and 1 min at 72° C., ending with a single final cycle of 12 min at 72° C. It will be appreciated by those skilled in the art that the PCR amplification conditions, particularly the hybridization temperature, will be easily selected based on the predicted or empirically determined $T_m$ of the primers. After amplification, 20 $\mu$l of each reaction was applied to a DNA denaturing polyacrylamide gel for electrophoretic separation and visualization of the $^{33}$P-labeled DNA by autoradiography using standard methods (Sambrook, J., et al., *Molecular cloning. A Laboratory Manual.*, 2nd ed., 1989).

Three independent but identical RD-PCR amplifications were performed for each reaction mixture, and the products were then separated in adjacent lanes of a polyacrylamide gel. In all cases, the identical reactions presented the same pattern in the RD-PCR fingerprint (i.e., there was no significant variation from tube to tube for a single source of mRNA and PCR primers). To provide size markers, a DNA sequencing ladder spanning a size range of about 100–600 base pairs (SequaMark™, Research Genetics) was separated on another lane of the gel.

The amplification products for unstimulated and hemin-stimulated K562 cells showed clear similarities and differences in mRNA expression. These differences were reproducible among three independent RD-PCR amplification reactions done for each combination of a given cell type and primer type. The mRNA was isolated from unstimulated and hemin-stimulated K562 cells. The PCR reactions were done using primers with two nesting bases (either 3'-AA or 3'-AT) in each PCR reaction, and the amplified DNA products were visually analyzed after electrophoretic separation on polyacrylamide gels. These primers represent two of the sixteen possible permutations of the two nesting bases. Approximately 50 to 100 fragments ranging in size from about 200 bp to about 550 bp were observed in each gel lane. In general, it was clear that different bands were produced by the 3'-AA and 3'-AT primers, as expected. In contrast, the stimulated and unstimulated cells showed relatively similar patterns of bands (although with a number of differences) for any given primer type. Prominent bands obtained for both stimulated and unstimulated cells with the 3'-AA primer included ones at about 540, 407, 298, 296, 254, and 242 bp.

Prominent differences included bands seen for the stimulated cells at about 477, 338, and 303 bp. Prominent bands obtained in both stimulated and unstimulated cells with the 3'-AT primer included ones at about 381, 340, 283, and 281 bp. Prominent differences included bands in the stimulated cells at about 530 and 255 bp.

The collections of fragments amplified using this procedure with a given primer set are here called amplicons. When used in all possible pairwise combinations, primers with two 3'-nesting bases divide the fragments into $4^2!/[(4^2-2)!\cdot 2!]=120$ different (though not mutually exclusive) amplicons. For primers with one nesting base, the corresponding number is $4^1!/[(4^1-2)!\cdot 2!]=10$, and for three nesting bases the number is $4^3!/[(4^3-2)!\cdot 2!]=2,026$. Because of the well-defined specificity produced using this method, RD-PCR with two or three nesting bases is useful for cataloguing disparate mRNA expression patterns and for differential analysis of closely related cells. To check for fragments resulting from incomplete restriction cutting and then amplified, the products can be re-cut with the original enzyme and by then electrophoresed side-by-side with product itself for comparison.

For further characterization, selected RD-PCR products were re-cut with the original enzyme, Sau3A I, and inserted into a pUC18 vector cut with BamH I for DNA sequencing.

EXAMPLE 4

A Kit for Detecting Differential Gene Expression

A kit is provided allowing those skilled in the art to use the method of the present invention to detect differential gene expression in cells or tissues.

The kit may include reagents for isolation of purified mRNA (i.e., buffers for lysis of cells, RNase-free DNase for digestion of DNA, and oligo-dT molecules attached to a solid matrix to allow isolation of poly-A containing mRNA) using methods well known in the art, in addition to those reagents specifically used for RD-PCR. Alternatively, the kit may contain only those reagents used for RD-PCR steps using mRNA already isolated by the user by any method of choice.

The kit contains reagents for cDNA synthesis, including a primer for first strand synthesis (an oligo-dT containing primer as described in Example 1), reverse transcriptase (RT) and appropriate buffers containing all four dNTP at concentrations well known in the art. The kit further includes reagents for synthesis of the cDNA second strand (including enzyme, either RT or Klenow DNA polymerase, and appropriate buffers containing the four dTNP) and for purifying the synthesized cDNA using methods well known to those skilled in the art.

The kit further contains restriction endonucleases for digestion of the double stranded cDNA (e.g., Sau3A I, EcoR I and BamH I) as described in Example 1, along with the appropriate buffers for the restriction digestions. Alternatively, the user may supply the buffers and restriction endonucleases of choice available from other sources. The kit also contains double stranded adaptor DNA sequences with an overhang appropriate to hybridizing to the ends of the cDNA fragments cut with the chosen restriction endonuclease (e.g., Sau3A I). DNA ligase and appropriate ligation buffer are provided.

The reagents for amplifying the cDNA by PCR are provided, including appropriate buffers, mixtures of the four dNTP, a thermostable DNA polymerase and sense and anti-sense primers appropriate for the adaptor sequence provided (e.g., the primers described in Example 1, either a limited selection or all possible oligomers for the combinations of 3' $X_1X_2$ and/or $_5Z_6$ bases in the primers).

Materials for separation and visualization of the RD-PCR products may be included in the kit. Alternatively, the user can use well known means of gel or automated separation and visualization chosen by the user. In addition, restriction endonucleases and appropriate vector DNA may be included in the kit to allow the use to clone the amplified RD-PCR products as desired. Control mRNA or cDNA and appropriate DNA size markers may also be included in the kit to aid the user in analysis of results obtained with the user's starting material.

The method of the present invention has numerous advantages over previously known mRNA differential display methods including the following.

(1) When exhaustive cutting by the restriction endonuclease is used, only one amplified band is detected per mRNA species present in the cell for the embodiment shown in FIG. 1. For the embodiment shown in FIG. 2, exhaustive cutting by the restriction endonuclease produces a well-defined number of bands for each mRNA species.

(2) The amplified fragments (i.e, the bands visualized) can be cloned directly into appropriately cut vectors because of the restriction endonuclease recognition sites available on the ends of the fragments, especially when using the embodiment shown in FIG. 2.

(3) The primers used in the PCR step can be optimized by appropriate design of the 3' and 5' adaptors, thus allowing hybridization at higher $T_m$ and eliminating or decreasing artifacts. Furthermore, primers can be designed as will readily be determined by those skilled in the art, and thus it is not necessary to rely on the oligo-dT sequence, which is generally suboptimal for PCR amplification because of the relatively low $T_m$ required for hybridization.

(4) Aside from the two 3' bases used to partition the mRNA products into separate sets, the sequences of the primers are all the same. Because of the overall similarity of the primers, it is possible to use essentially one set of PCR conditions for all partitions of the mRNA. Because the same PCR conditions can be used for all of the reactions, the possibility of visualizing artifactual differences in the fingerprints due to different reaction conditions is significantly decreased. Thus the precision and accuracy of the fingerprint obtained is increased. The ability to perform all PCR reactions under the same conditions also eases the use of the method, particularly when provided in a kit.

(5) Greater certainty of correct hybridization is achieved even though the initial selection of the cDNA subset relies only on the one, two or more nesting bases incorporated into the primer or primers. In contrast, in other differential display methods, PCR primers of ten or more nucleotides must be used for hybridization even though the specificity of hybridization corresponds to only that of about a six nucleotide primer.

(6) At least ten specific bases of known sequence used in priming the PCR amplifications can be used to identify amplified bands as fragments corresponding to parts of known mRNA sequences. For one nesting base, the number is ten, for two nesting bases, the number is twelve, and so on. All that is required is that the sequence to be identified be known, and known sequence can include a 3' untranslated region of mRNA. Because of the availability of cDNA sequences in databases, this information lends considerable power to the method for detection of known gene sequences.

The critical bases for comparison to known gene sequences using the embodiment shown in FIG. 2 include (i) the bases of the restriction endonuclease recognition sequence (e.g., the four bases of the Sau3A I recognition site), (ii) the one, two or three nested bases at each end of the amplified DNA fragment. These bases (or their complement) are then compared to known sequences, thus allowing for identification of a band corresponding to known gene sequence(s). For example, a sequence "GATCX$_1$X$_2$" provides discrimination of $4^6$ and when combined with the possible combinations at the other end, the discrimination information for identification is $4^{12}$ if only one primer type is used. This information plus the molecular size of the amplified fragment on a polyacrylamide gel would often suffice for presumptive identification of a band as being part of a known sequence.

The RD-PCR method disclosed is useful for characterizing cells based on their mRNA content, for representing expressed genes, and for discovery of therapeutics that alter cellular gene expression. The method is also useful for characterizing cells of a variety of types and under a variety of physiological conditions. For example, the method can be used to distinguish cells of different types (myocardial cells compared with smooth muscle cells) or cells of different types within the same tissue (adrenal medullary cells compared with adrenal cortex cells). Cells of the same type but in different physiological states can be characterized and distinguished by use of the method, including distinguishing malignantly transformed cells from normal cells, characterizing cells of the immune system following activation by an immunogen or regulatory factor, and characterizing cells undergoing developmental changes. When the components used in the method are provided in a kit, it can be a useful diagnostic tool for characterizing cells based on their mRNA content (e.g., for determining if cells from a biopsy are malignant or normal). Because it can be used to monitor the physiological status of cells, the method is useful for discovery of new therapeutics to prevent diseases and improve the current treatments of a variety of pathological conditions. That is, efficacy of a therapeutic treatment can be monitored by characterizing cells before and after treatment using the RD-PCR method. As such, the method is useful for drug discovery, especially for initial testing of anti-cancer or anti-viral drugs in vitro. The method is also useful for identifying cells or tissue from particular individuals or species based on the fingerprint obtained from the mRNA content of isolated cells or tissue and comparing it to cells or tissue from a known source.

Although preferred embodiments have been described in the foregoing description and examples, the scope of the invention is defined by the claims that follow and all equivalents thereof.

What is claimed is:

1. A method for characterizing mRNA molecules in a population of mRNAs including the steps of providing purified and isolated mRNA molecules, reverse transcribing a double stranded cDNA from said isolated mRNA molecules, digesting said double stranded cDNA with a restriction endonuclease to produce cDNA fragments in which either one end or both ends of said cDNA fragments have a sequence that specifically hybridizes to adaptor DNA sequences, wherein the improvement comprises:

after said digesting step, hybridizing adaptor DNA sequences to said cDNA fragments in which both ends of said cDNA fragments have a sequence that specifically hybridizes to said adaptor DNA sequences;

ligating said adaptor DNA sequences to said cDNA fragments having hybridized adaptor DNA sequences;

amplifying said cDNA fragments having ligated adaptor DNA sequences by a polymerase chain reaction (PCR) with primer DNA sequences that hybridize to the ends of said cDNA fragments having ligated adaptor DNA sequences, wherein said primer DNA sequences have at least one nucleotide at the 3' end that specifically hybridizes to a subset of cDNA molecules produced during said reverse transcribing step, thereby producing amplified cDNA fragments; and detecting the presence of the amplified cDNA fragments, wherein each amplified cDNA fragment corresponds to a mRNA molecule within said population of mRNAs, thereby characterizing mRNA molecules in a population of mRNAs.

2. A method for characterizing mRNA molecules in a population of mRNAs including the steps of providing purified and isolated mRNA molecules, reverse transcribing a double stranded cDNA from said isolated mRNA molecules, digesting said double stranded cDNA with a restriction endonuclease to produce cDNA fragments in which at least one end of said cDNA fragments has a sequence that specifically hybridizes to an adaptor DNA sequence, wherein the improvement comprises:

after said digesting step, hybridizing adaptor DNA sequences to said cDNA fragments in which at least one end of said cDNA fragments has a sequence that specifically hybridizes to said adaptor DNA sequences;

ligating said adaptor DNA sequences to said cDNA fragments having hybridized adaptor DNA sequences;

amplifying said cDNA fragments having ligated adaptor DNA sequences by a polymerase chain reaction (PCR) with primer DNA sequences that hybridize to the ends of said cDNA fragments having ligated adaptor DNA sequences, wherein said primer DNA sequences have at least one nucleotide at the 3' end that specifically hybridizes to a subset of cDNA molecules produced during said reverse transcribing step, thereby producing amplified cDNA fragments; and detecting the presence of the amplified cDNA fragments, wherein each amplified cDNA fragment corresponds to a mRNA molecule within said population of mRNAs, thereby characterizing mRNA molecules in a population of mRNAs, and wherein the improvement further comprises, in said reverse transcribing step, priming said isolated mRNA molecules to produce a first strand of cDNA with a primer DNA sequence which comprises, in a 5' to 3' orientation, a 5'-adaptor DNA sequence;

one or more nucleotides adjacent to said 5'-adaptor DNA sequence;

an oligo-dT sequence; and one or more nucleotides adjacent to said oligo-dT sequence, wherein the nucleotide directly adjacent to said oligo-dT sequence can be C, A or G but not T, and nucleotides 3' of the nucleotide directly adjacent to said oligo-dT sequence can be C, A, G or T, and wherein said nucleotides adjacent to said oligo-dT sequence specifically hybridize to ribonucleotides occurring 5' of a poly-(A) sequence In mRNA molecules; and synthesizing a second strand of cDNA complementary to said first strand of cDNA.

3. The method of claim 1, or 2, wherein said detecting step comprises a step of cloning said amplified cDNA fragments in a vector.

4. The method of claim 1 or 2, wherein said detecting step comprises a step of sequencing said amplified cDNA fragments.

5. The method of claim 1 or 2, wherein said amplifying step further comprises hybridizing said primer DNA sequences at a stringent hybridization temperature determined from the melting temperatures ($T_m$) of said primer sequences.

6. The method of claim 2, wherein said amplifying step comprises priming said cDNA fragments having ligated adaptor DNA sequences with a first primer DNA sequence which comprises, in a 5' to 3' orientation, a DNA sequence complementary to said 5'-adaptor DNA sequence which is employed in said reverse transcribing step, and at least one nucleotide that specifically hybridizes to said subset of cDNA molecules produced during said reverse transcribing step, and further comprises priming said cDNA fragments having ligated adaptor DNA sequences with a second primer DNA sequence comprising, in a 5' to 3' orientation, a sequence complementary to one strand of said ligated adaptor DNA sequences and at least one nucleotide that specifically hybridizes to said subset of cDNA molecules produced during said reverse transcribing step.

7. The method of claim 1 or 2, wherein said detecting step comprises steps of digesting said amplified cDNA fragments with at least one restriction endonuclease that specifically cuts said amplified cDNA fragments at a restriction endonuclease recognition site which is present in one or more of said primer DNA sequences employed in said amplifying step and which is located in said amplified cDNA fragments, thereby producing digested cDNA fragments, and cloning said digested cDNA fragments into a vector.

8. The method of claim 1 or 2, wherein said restriction endonuclease which is employed in said digesting step produces at least a one-nucleotide overhang at ends of said cDNA fragments after digestion is complete.

9. The method of claim 1 or 2, wherein said primer DNA sequences having at least one nucleotide at the 3' end that specifically hybridizes to a subset of cDNA molecules have one, two or three nucleotides at the 3' end that specifically hybridize to said subset of cDNA molecules.

10. The method of claim 9, wherein said primer DNA sequences having one, two or three nucleotides at the 3' end that specifically hybridize to a subset of cDNA molecules are a mixture of primer DNA sequences that vary at the one, two or three nucleotides at the 3' end in a primer in said mixture with respect to the one, two, or three nucleotides at the 3' end in other primers in said mixture.

11. The method of claim 9, wherein said amplifying step further comprises a sequential amplification reaction in which the first ten to twenty-five cycles are performed with primer DNA sequences having one nucleotide at the 3' end that specifically hybridizes to said subset of cDNA molecules, and subsequent cycles are performed with primer DNA sequences having two or three nucleotides at the 3' end that specifically hybridize to said subset of cDNA molecules.

12. The method of claim 1 or 2, further comprising a step of comparing the sequences of said amplified cDNA fragments with known DNA sequences.

13. The method of claim 12, wherein said comparing step comprises conducting a computer search for known DNA sequences that possess a first restriction endonuclease recognition site, wherein said site is present in one or more of said primer DNA sequences employed in said amplifying step and wherein said site is located in said primer DNA sequences 5' of and adjacent to said at least one nucleotide at said 3' end of said primer DNA sequences that specifically hybridizes to said subset of cDNA molecules, and wherein said comparing step further comprises conducting a computer search for a subset of said known DNA sequences having a size approximately the same as the size of said amplified cDNA fragments, wherein the size of said known DNA sequences is determined by the distance between said first restriction endonuclease recognition site and a second restriction endonuclease recognition site.

* * * * *

UNITED STATES PATENT AND TRADEMARK OFFICE
CERTIFICATE OF CORRECTION

PATENT NO.    : 6,270,966 B1
DATED         : August 7, 2001
INVENTOR(S)   : John N. Weinstein and John Buolamwini It is certified that error appears in the above-identified patent and that said Letters Patent is hereby corrected as shown below:

<u>Column 34,</u>
Line 55, please delete the first word of line 55: "further".

Signed and Sealed this

Twentieth Day of August, 2002

Attest:

JAMES E. ROGAN
Attesting Officer    Director of the United States Patent and Trademark Office